United States Patent
Hoenes

(10) Patent No.: US 8,734,365 B2
(45) Date of Patent: May 27, 2014

(54) TEST ELEMENT MAGAZINE HAVING COVERED TEST FIELDS

(75) Inventor: Joachim Hoenes, Zwingenberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/212,737

(22) Filed: Aug. 18, 2011

(65) Prior Publication Data

US 2012/0039772 A1 Feb. 16, 2012

Related U.S. Application Data

(63) Continuation of application No. PCT/EP2010/000866, filed on Feb. 12, 2010.

(30) Foreign Application Priority Data

Feb. 19, 2009 (EP) .................................... 09153209

(51) Int. Cl.
*A61B 5/00* (2006.01)
*B65D 81/00* (2006.01)

(52) U.S. Cl.
USPC .......................................... 600/584; 600/583

(58) Field of Classification Search
USPC ........... 600/573, 575, 583, 584; 606/181, 182
See application file for complete search history.

(56) References Cited

U.S. PATENT DOCUMENTS

| | | | |
|---|---|---|---|
| 5,443,080 A * | 8/1995 | D'Angelo et al. | 600/573 |
| 6,036,924 A | 3/2000 | Simons et al. | |
| 6,251,083 B1 * | 6/2001 | Yum et al. | 600/584 |
| 7,288,073 B2 | 10/2007 | Effenhauser et al. | |
| 7,553,615 B2 | 6/2009 | Heindl et al. | |
| 7,959,581 B2 | 6/2011 | Calasso et al. | |
| 8,234,767 B2 | 8/2012 | Roeper et al. | |
| 8,303,518 B2 | 11/2012 | Aceti et al. | |
| 2002/0087056 A1 | 7/2002 | Aceti et al. | |
| 2002/0120216 A1 | 8/2002 | Fritz et al. | |
| 2002/0188224 A1 | 12/2002 | Roe et al. | |
| 2003/0191415 A1 | 10/2003 | Moerman et al. | |

(Continued)

FOREIGN PATENT DOCUMENTS

| DE | 19819407 A1 | 11/1999 |
|---|---|---|
| EP | 1360932 A1 | 11/2003 |

(Continued)

OTHER PUBLICATIONS

Banauch et al., A glucose dehydrogenase for glucose determination in body fluids, Z. Klin. Chem. KLin. Biochem, vol. 13, 1975, pp. 101-107.

(Continued)

*Primary Examiner* — Max Hindenburg
*Assistant Examiner* — Adam Eiseman
(74) *Attorney, Agent, or Firm* — Harness, Dickey

(57) ABSTRACT

An analytic magazine is proposed, which comprises at least one chamber with at least one analytic aid. The analytic aid comprises at least one test element for detecting at least one analyte in a sample of a bodily fluid. The test element has at least one test field with at least one test chemical. The test field is at least partly arranged within the chamber, wherein at least one wall of the chamber at least partly covers the test field and at least partly delimits a test-field surface that is accessible from the chamber.

17 Claims, 5 Drawing Sheets

(56) References Cited

U.S. PATENT DOCUMENTS

| | | |
|---|---|---|
| 2003/0199909 A1* | 10/2003 | Boecker et al. ............... 606/181 |
| 2003/0212347 A1 | 11/2003 | Sohrab |
| 2003/0212423 A1* | 11/2003 | Pugh et al. .................... 606/181 |
| 2004/0034318 A1 | 2/2004 | Fritz et al. |
| 2004/0092842 A1* | 5/2004 | Boecker et al. ............... 600/575 |
| 2004/0098009 A1 | 5/2004 | Boecker et al. |
| 2004/0102803 A1 | 5/2004 | Boecker et al. |
| 2005/0027211 A1 | 2/2005 | Kuhr et al. |
| 2005/0033340 A1 | 2/2005 | Lipoma et al. |
| 2005/0214891 A1 | 9/2005 | Horn et al. |
| 2006/0008389 A1 | 1/2006 | Sacherer et al. |
| 2006/0161078 A1 | 7/2006 | Schraga |
| 2006/0178600 A1 | 8/2006 | Kennedy et al. |
| 2006/0184064 A1 | 8/2006 | Paasch et al. |
| 2006/0200044 A1 | 9/2006 | Freeman et al. |
| 2006/0264996 A1 | 11/2006 | LeVaughn et al. |
| 2007/0016103 A1 | 1/2007 | Calasso et al. |
| 2007/0100255 A1 | 5/2007 | Boecker et al. |
| 2007/0129650 A1 | 6/2007 | Freeman et al. |
| 2007/0142748 A1 | 6/2007 | Deshmukh et al. |
| 2007/0142854 A1 | 6/2007 | Schraga |
| 2007/0167872 A1 | 7/2007 | Freeman et al. |
| 2007/0173741 A1 | 7/2007 | Deshmukh et al. |
| 2007/0292314 A1 | 12/2007 | Effenhauser et al. |
| 2008/0021346 A1* | 1/2008 | Haar et al. .................... 600/583 |
| 2008/0039887 A1 | 2/2008 | Conway et al. |
| 2008/0040919 A1 | 2/2008 | Griss et al. |
| 2008/0094804 A1 | 4/2008 | Reynolds et al. |
| 2008/0103415 A1 | 5/2008 | Roe et al. |
| 2008/0213809 A1 | 9/2008 | Heindl et al. |
| 2008/0243032 A1 | 10/2008 | Hindelang et al. |
| 2008/0294068 A1 | 11/2008 | Briggs et al. |
| 2008/0300509 A1 | 12/2008 | Hoenes et al. |
| 2009/0010802 A1 | 1/2009 | Joseph et al. |
| 2009/0093695 A1* | 4/2009 | Nakamura et al. ............ 600/347 |
| 2009/0099477 A1 | 4/2009 | Hoenes et al. |
| 2009/0099585 A1 | 4/2009 | Conway et al. |
| 2009/0192411 A1 | 7/2009 | Freeman |
| 2009/0204025 A1 | 8/2009 | Marsot et al. |
| 2010/0010375 A1 | 1/2010 | Haar et al. |
| 2010/0185120 A1 | 7/2010 | Sacherer et al. |
| 2010/0222799 A1 | 9/2010 | Roeper et al. |
| 2010/0234869 A1 | 9/2010 | Sacherer |
| 2011/0143416 A1 | 6/2011 | Horn et al. |
| 2012/0041339 A1 | 2/2012 | Kuhr et al. |
| 2012/0063970 A1 | 3/2012 | List et al. |

FOREIGN PATENT DOCUMENTS

| | | |
|---|---|---|
| EP | 1360935 A1 | 11/2003 |
| EP | 1900321 A1 | 3/2008 |
| EP | 1929937 A1 | 6/2008 |
| EP | 1997429 A1 | 12/2008 |
| EP | 2042098 A1 | 4/2009 |
| EP | 2050392 A1 | 4/2009 |
| WO | 0164105 A1 | 9/2001 |
| WO | 02101343 A2 | 12/2002 |
| WO | 03070099 A1 | 8/2003 |
| WO | 03088834 A1 | 10/2003 |
| WO | 2005065414 A2 | 7/2005 |
| WO | 2005104948 A1 | 11/2005 |
| WO | 2006031920 A2 | 3/2006 |
| WO | WO 2007001003 A1 * | 1/2007 |
| WO | 2008145625 A2 | 12/2008 |
| WO | 2009036986 A2 | 3/2009 |

OTHER PUBLICATIONS

Bergmeyer, Methoden der enzymatischen Analyse (Methods of enzymatic analysis), Verlag Chemie, 2nd edition, 1970, p. 417.
Hoenes et al., The Technology Behind Glucose Meters: Test Strips, Diabetes Technology & Therapeutics, vol. 10, Supplement 1, 2008, pp. S-10-S26.

* cited by examiner

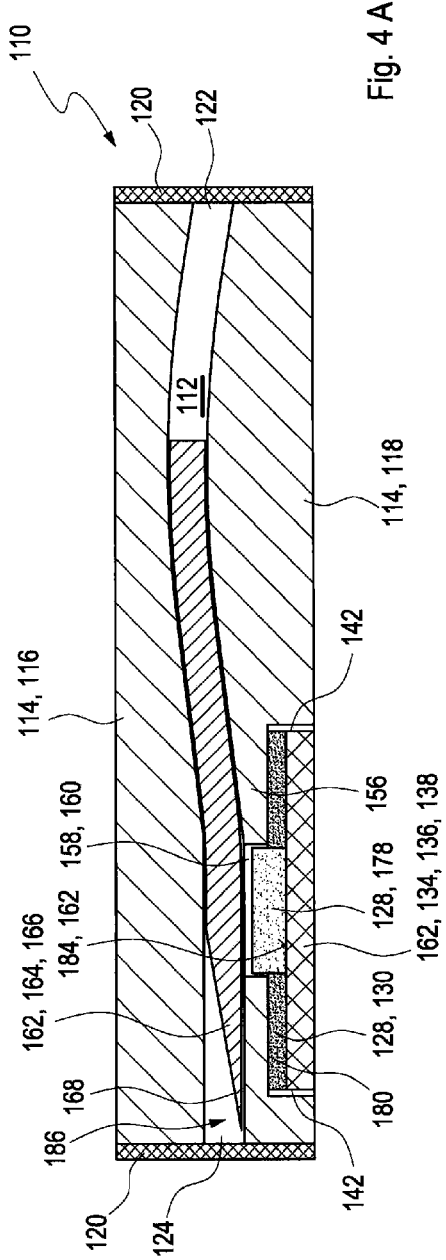
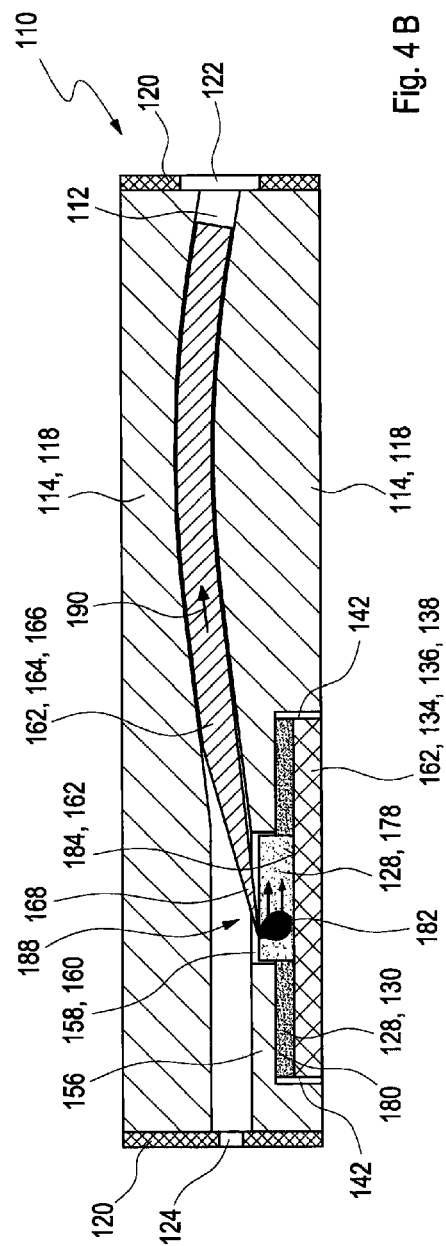

TEST ELEMENT MAGAZINE HAVING COVERED TEST FIELDS

CROSS-REFERENCE TO RELATED APPLICATIONS

This application is a continuation of International Application No. PCT/EP2010/000866, filed on Feb. 12, 2010, which claims the benefit and priority of European Patent Application No. 09153209.3, filed on Feb. 19, 2009. The entire disclosures of the above applications are incorporated herein by reference.

BACKGROUND

The invention relates to an analytic magazine with at least one analytic aid. Such analytic magazines with analytic aids are used, in particular, in the field of medical diagnostics in order to detect one or more analytes in a sample of a bodily fluid. In particular, such analytic magazines can be used in integrated analytic systems, which provide both a sample-taking function and the aforementioned function of detecting at least one analyte in a bodily fluid. In principle, other applications are also possible, for example applications outside the field of medical diagnostics. In the following text, the invention is substantially described with reference to detecting blood glucose, without restricting further possible applications.

Systems by means of which analytes can be detected in samples are known, in particular, from the field of medical diagnostics, but also from other fields in the natural sciences, medicine and technology. Within the scope of medical diagnostics, a detection such as this, for example of blood glucose, generally comprises the generation of a sample of bodily fluid, for example blood or interstitial fluid, followed by holding this sample and qualitative and/or quantitative analysis. To this end, use is generally made of one or more analytic aids, which can for example comprise a lancet and/or test elements, by means of which the sample can be generated and/or held and/or analyzed.

In the past, the integration of various system functions in particular has led to commercial solutions with replaceable magazines for the analytic aid, e.g. test-strip magazines, in such analytic systems, e.g. blood-glucose measurement systems. Typical exponents of this product group are the Accu-Chek Compact® and Ascensia Breeze systems, which represent commercially available systems. Typical associated magazines generally hold 17 or 10 test strips.

In the latest systems, different system functions are often combined in an integrated fashion, for example the system function of generating a sample (for example by perforating an area of the skin) and the system function of holding a sample and also, optionally, the system function of analyzing it. When designing more integrated systems, it may for example be possible to combine the step of obtaining blood with a test function. By way of example, so-called "microsamplers" are known for this purpose, and these can combine the function of a lancet and the function of transporting the sample, for example to a test element. Hence, it is possible to dispense with a separate puncturing aid for withdrawing blood, for example from a finger pulp, an ear lobe or any another area of skin of a subject.

In general, an analytic system can house a plurality of analytic aids, for example a plurality of microsamplers, in a fixedly integrated magazine or in various types of replaceable magazine. In principle, irrespective of the type of analytic aid, it is possible to distinguish between three main types of analytic magazines; to be precise, it is possible to distinguish between round magazines (for example in the shape of drums and/or disks), linear magazines (for example in the form of stacked magazines, zigzag magazines, or the like), and tape magazines, in which the analytic aid is arranged on a tape or another type of at least partly flexible support. In principle, these types of magazine may also be used or modified within the scope of the invention described below. In the prior art, round magazines are described in, for example, US 2006/0008389, US 2007/0292314, US 2006/0184064, US 2003/0212347, or US 2002/0087056. By way of example, linear magazines are described in U.S. Pat. No. 6,036,924 or in US 2003/0191415. By way of example, tape magazines are disclosed in US 2002/0188224, in US 2008/0103415, in EP 1360935 A1, or in DE 19819407 A1.

Hence, in addition to separate magazines for lancets and test elements, which contain a test chemical, magazines are established within the scope of the above-described integration that hold both test elements and lancets, for example in the form of so-called combined disposables. These aids can be stored in the magazine in a desired quantity, and the magazine can be inserted into a corresponding instrument, which is also referred to as an analytic system in the following text. However, such designs generally lead to rather complex, large systems. Even the housing of test elements such as test fields and lancets on tape, for example within the scope of so-called "lancet-on-tape" systems, has the disadvantage that functionally relevant parts firstly have to be isolated during production and then have to be reapplied to a tape.

A further technical challenge of combined magazines, which store analytic aids comprising both lancets and test elements, more particularly with a test chemical, consists of the stringent requirements in respect of the biocompatibility of the analytic aid. In particular, the test chemical used in the test elements can comprise e.g. enzymes and/or other materials, e.g. auxiliary materials, that can lead to incompatibility when in direct contact with body tissue of a subject. Although such phenomena have not yet been examined in precise detail, it would for example be feasible that certain enzymes cause allergic reactions in the subject. Hence, even in the case of integrated systems and appropriate magazines for integrated systems, care has to be taken that, in addition to a simple and cost-effective production, the biocompatibility of such systems is always ensured.

Thus, by way of example, WO 2006/031920 A2 and WO 2005/065414 A2 each disclose systems and methods for taking a sample. In the process, a puncturing element in each case pierces a test element before the puncturing element penetrates an area of skin of a user. When the puncturing element is withdrawn, the sample adhering to the puncturing element is applied to the test element from the outside. However, a disadvantage in this case is that parts of the test chemical can already adhere to the puncturing element during the forward motion of said puncturing element, i.e. during the puncturing process, when the test element is pierced and hence this can lead to undesirable ingress of a test chemical into the body of the subject.

WO 01/64105 A1 similarly discloses a device for detecting an analyte and determining the amount thereof. In this device, provision is also made for a lancet to pierce a test field during a sample-taking procedure and wipe bodily fluid onto the test field from the outside when said lancet is retracted from the body tissue of the user. The above-described problems of possible ingress of a test chemical into the body tissue also occur in this arrangement.

Furthermore, a problem that frequently occurs in the aforementioned devices, and also in other known devices, is that the edges of the test fields in particular can tend to fall apart. By way of example, this can lead to components of the test chemical breaking off the edges of the test fields and reaching the lancet.

SUMMARY

Hence, it is an object of the present invention to provide an analytic magazine that solves the aforementioned technical challenges of known magazines. In particular, the analytic magazine should also be suitable for use in integrated systems and should be able to be produced in a cost-effective fashion, whilst at the same time ensuring the above-described biocompatibility.

This object is achieved by the invention with the features of the independent claims. Advantageous developments of the invention, which can be implemented individually or in combination, are illustrated in the dependent claims.

The present invention proceeds from the discovery that while analytic aids, which can comprise both a lancet and a test element, are stored within the same magazine chamber of an analytic magazine, the test chemical of the test element may, under certain circumstances, contaminate the lancet, e.g. a needle tip. Hence, as illustrated above, parts of the test chemical for example can penetrate the skin of a patient during a piercing procedure. Proceeding from this discovery, the invention illustrated below is substantially based on the idea that, in the dry state of the test chemical, particulate components of the test chemical in particular may contaminate further components of the analytic aid, e.g. a lancet. Such particulate components, for example particles, particle conglomerates, or "crumbs", can be produced even in the case of very careful production by means of various processes. Thus, test fields with the appropriate test chemical for example are often produced by cutting methods; this is explained in more detail below. Such corresponding particulate contaminants can occur at cutting edges. Furthermore, particles can also be released within the scope of operating the analytic magazines, for example by vibrations or mechanical abrasions. In particular, this may occur when test fields come into contact with further elements, for example further partial aids, more particularly the aforementioned lancets themselves.

The invention presented in more detail below is based on the common inventive idea of avoiding such contaminations, more particularly contaminations by particulate contaminants, by applying appropriate protective measures. In particular, according to the invention, the possibility of transferring such contaminants onto optional lancets should be prevented. Accordingly, provision can be made for one or more elements, which act as separation elements and are designed firstly to prevent, at least to a large extent, transfer of contaminants from test elements to other parts of the analytic aid, more particularly lancets stored in the same chamber, more particularly the transfer of particles, and secondly to allow at least partial access of the sample to a test chemical of the test element, for example access of a blood sample and/or constituents of this blood sample to the test chemical.

Proceeding from this common concept, a first aspect of the invention proposes an analytic magazine that comprises at least one chamber with at least one analytic aid. The analytic aid comprises at least one lancet.

Here, in general terms, an analytic magazine is understood to be a device, preferably a compact, overall integral device, which can be used for use in an analytic system for detecting at least one analyte in a sample of a bodily fluid. By way of example, reference can be made to the application examples illustrated above. By way of example, the analytic magazine can accordingly have one of the known magazine shapes. Hence, the analytic magazine can for example be embodied as a round magazine, more particularly as a drum magazine and/or disk magazine, as a tape magazine or as a stick magazine. The analyte can, more particularly, be at least one metabolite and/or another physically and/or chemically detectable property of the sample of the bodily fluid, such as, for example, blood glucose, cholesterol, coagulates or the like.

In general, a chamber should be understood to mean a receptacle, in which at least one analytic aid is held, either in its entirety or in part. In the process, the chamber can have at least one interior space, wherein provision can also be made for a plurality of interior spaces, which can have a contiguous embodiment or a separate embodiment. The at least one chamber can have a closed-off design, but it can also be at least partly opened, i.e. it can have at least one opening. By way of example, the chamber can be formed in a housing and/or housing part of the analytic magazine, wherein chamber walls, which delimit and/or define the chambers, can be formed in the housing. The analytic magazine may comprise one or, preferably, more of such chambers. Analytic magazines with at least 10 chambers, preferably at least 20 chambers, at least 25 chambers, or with even more than 50 chambers are particularly preferred.

Here, an analytic aid can be understood to mean any aid that can be used for qualitative and/or quantitative detection of the at least one analyte in the sample of the bodily fluid and/or can support such a detection. If a plurality of chambers are provided, at least one of the analytic aids is preferably held in each chamber. Each of these analytic aids can in turn be assembled from a number of partial aids. The analytic aids can be wholly or partly held within the chambers, and so, for example, parts of the analytic aids can also be arranged outside of the chambers, for example partial aids of the analytic aids. In particular, the term being held in a chamber should also include the case where the aids are wholly or partly integrated into chamber walls of the chambers, more particularly into the housing and/or housing part, or are connected to this housing and/or housing part, wherein the latter should be accessible from the interior space of the chamber.

In the proposed analytic magazine, the at least one analytic aid in each case comprises at least one lancet. By way of example, this lancet can be embodied as a simple lancet needle or as a lancet blade. However, it is particularly preferred if the at least one lancet furthermore comprises at least one collection element, more particularly a capillary element, for collecting and/or transporting the sample. Accordingly, the at least one lancet can more particularly be wholly or partly embodied as a microsampler. Moreover, the at least one analytic aid can comprise further types of analytic aids and/or partial aids. Thus, the analytic aid can furthermore comprise one or more of the following aids: a transfer element for transferring a sample from the skin of a subject to a test element; a test element with at least one test chemical. In this case, as described above, the analytic aid may be assembled from a plurality of partial aids, which can be interconnected but which can also be embodied independently from one another, for example they can be arranged independently of one another. Hence, for example, at least one partial aid can be mounted in the chamber in a movable fashion whereas at least one further partial aid is held in a substantially fixed fashion in the chamber. By way of example, provision can be made for a movably mounted lancet, as a partial aid, and a substantially immovably mounted test element.

Here, in general terms, a lancet should be understood to mean an element that is designed to generate at least one opening, for example a puncture and/or a cut, in a tissue of a subject, for example in the skin of a subject. To this end, the lancet can, for example, comprise a tip and/or a blade. More particularly, the lancet may be embodied as a round lancet and/or as a flat lancet, the latter for example as a result of an appropriate production from a metal band, for example by means of an etching process.

A microsampler should be understood to mean a combination of a lancet and a capillary element, for example a capillary and/or a capillary gap, wherein the capillary element is designed to hold the sample, at least in part, and/or to transfer it, using capillary forces in the process. In this respect, the capillary element can, for example, also wholly or partly act as a transfer element. Alternatively, or in addition thereto, it is also possible for provision to be made for other types of transfer or transport elements, for example movable transfer elements or the like.

A test element should be understood to mean an element that has at least one test chemical, by means of which the qualitative and/or quantitative detection of the at least one analyte can be carried out. More particularly, the test chemical can be embodied to change one or more physically and/or chemically detectable properties if the at least one analyte is present, for example a property, more particularly a color property, that can be measured by optical means and/or a property that can be detected by electrochemical means. In respect of possible embodiments of the test chemical, reference may be made to e.g. J. Hoenes et al., Diabetes Technology & Therapeutics, Volume 10, Supplement 1, 2008, S-10-S-26. Furthermore, reference may be made to WO 2007/012494 A1 (see also, US 2008/0213809). Particularly moisture-stable test chemicals are described therein. The test chemicals cited in these documents may, individually or in combination, also be used within the scope of the present invention. In particular, use can be made of very specific test chemicals, in which the detection reacts specifically to the at least one analyte.

The test element comprises at least one test field with at least one test chemical, which is at least partly arranged within the chamber. By way of example, the test field can be integrated into the chambers and/or the magazine, for example into a chamber wall and/or a housing. Thus, the test field can for example form part of the chamber wall, i.e. delimit the chamber in at least one direction.

A test chemical should in general be understood to mean a material that, as described above, changes at least one detectable property, e.g. a physical and/or chemical property, if the at least one analyte to be detected is present. In particular, these changes in property may occur in a specific fashion, i.e. only if the at least one analyte to be detected is present and not, or merely to a much lesser extent, if other substances are present. However, in the process, it is possible to tolerate property changes that occur in the presence of substances that, with a high degree of certainty, are not contained in the sample, or merely in negligible concentrations.

The term test field should be understood to mean a contiguous amount of the test chemical, applied to a certain area. By way of example, the test field may comprise a layer or a region of a layer of the test chemical, which may for example be applied to a support. By way of example, the layer may be embodied as a continuous layer, which in turn may also be composed of one or more partial layers. By way of example, the layer may have a constant thickness. The layer may be continuous, or else it can have one or more openings. Here, the optional support however is itself not part of the test field; rather, the term test field only refers to the test chemical and, optionally, to auxiliary materials and/or auxiliary layers, such as e.g. an optional separation layer or the like, connected to the test chemical. Hence the test field provides the amount of material that is involved in the actual detection, and not, for example, elements serving only for mechanical stabilization, such as e.g. a support.

A test-field surface should be understood to mean the surface of the test field that is accessible for placing the sample. By way of example, if the test field is applied to a support, placing the sample may for example be made possible on the surface of the test field facing away from the support, and so this surface may be used as sample-placing surface and hence as test-field surface. However, as will be explained in more detail below, this surface may, wholly or partly, be spatially covered by additional elements, for example a frame, and so merely part of this surface may be accessible for placing a sample. In that case, it is merely this accessible part that should be referred to as test-field surface. By way of example, as will be explained in more detail below, this can be carried out through a wall in the chamber that has one or more openings, wherein the sample, which is in the chamber, is placed onto the test field through the opening, and so merely the part of the test field visible through the opening from the chamber, or the surface of this region, serves as a sample-placing surface and hence as a test-field surface. This is explained in more detail below in an exemplary fashion.

Hence, the term test element should in general be understood to mean an element that has at least one test field with at least one test chemical. The test element may, optionally, for example comprise one or more supports, for example a substrate film or the like, for example a support made of a plastic material, a paper material, a ceramic material, or a combination of the aforementioned and/or other materials. However, in principle, test elements with test fields in the form of free-standing test-chemical films are also feasible.

As illustrated above, the term an arrangement within the chamber should in general comprise the test field, more particularly the test-field surface thereof, being accessible from the chamber, in particular for the sample of the bodily fluid and/or components of the sample. In particular, accessibility should be understood to mean that a sample in the interior of the chamber can be applied to the test field and/or that it can be applied thereon from the interior of the chamber. The test field and, more particularly, at least one test-field surface of this test field, i.e. a surface onto which the sample can be applied, should thus be connected to the interior of the chamber such that a sample can be applied onto the test-field surface from the interior of the chamber, in contrast, for example, to placing the sample from the outside, outside of the chamber. In particular, the sample can be applied by a direct transfer of the sample from the lancet to the test-field surface. By way of example, to this end the lancet may, at least temporarily, be held in the chamber again after a puncturing process such that there is such spatial proximity between the held sample, which may for example be held directly on the lancet and/or in an optional capillary, for example in a capillary gap, that is connected to the lancet, that there may at least in part be a transfer of the sample to the test-field surface. However, alternatively, or in addition thereto, provision may also be made for aids, for example within the analytic magazine and/or in an analytic system using the analytic magazine, which simplify the transfer of the sample from the lancet to the test-field surface. By way of example, provision can be made for at least one actuator, which temporarily presses the lancet and/or the capillary gap onto the test-field surface or brings it into the vicinity of the latter. In yet another alternative, or in addition thereto, the chamber walls for example can have an arced design to ensure that the lancet flexes such that the transfer can take place. Various embodiments are possible.

By way of example, the test field may be mounted entirely within the chamber, or else it can wholly or partly be integrated into a housing of the analytic magazine and/or into a housing part of this housing. In order to make the test field accessible, an opening and/or a recess and/or a blind hole may for example be provided in a chamber wall and/or in a housing of the analytic magazine, through which opening and/or indentation and/or blind hole the sample of the bodily fluid and/or components of the sample of the bodily fluid can reach the test field; this was already partly explained above and will be explained in more detail below. By way of example, the at least one opening may comprise at least one through-opening in the wall of the chamber, i.e. an opening through which the interior of the chamber is accessible from outside the magazine, provided that the test field has not been applied to this opening.

According to the invention, it is proposed that a wall of the chamber at least partly covers the test field and thereby at least partly delimits a test-field surface of the test field for placing the sample, which test-field surface is accessible from the chamber. Here, a delimitation should in general be understood to be an arrangement in which the test-field surface directly adjoins the wall of the chamber in at least one dimension, preferably in two dimensions. By way of example, if the test element has at least one support onto which the at least one test field with the at least one test chemical is applied, it may for example be possible, as explained above, for a surface of the test field facing away from the support, including a distributor element and/or separation element possibly applied to this surface, to be used for placing a sample. In the case of delimitation by the wall of the chamber, as proposed according to the invention, this surface is however delimited by the wall of the chamber in at least one dimension, for example by this surface partly being covered by the wall of the chamber and partly being exposed. The exposed region, which then is still accessible for placing the sample from the chamber, then is the test-field surface within the scope of the present invention. As explained above, this may for example be a partial region of the surface that is visible from the chamber through an opening in the chamber wall and accessible for placing a sample.

In this respect, the proposed magazine, inter alia, differs from, for example, the arrangement described in WO 2006/031920 A2 and WO 2005/065414 A2, in which a sample is applied from the outside by there being a transfer of the sample to a tissue from the outside when the piercing element is pulled back, and this subsequently ensuring a distribution on detection surfaces. By contrast, in the magazine according to the invention, there can be an application of the sample from the interior of the chamber. The test chemical and the lancet can be spatially separate throughout the entire sample-taking process, and so ingress of test chemicals into the body tissue of the user can be entirely avoided. At the same time, as will be explained in more detail below, the possible integration of the test field into the chamber wall makes a much more simplified production possible.

By way of example, the test-field surface can be delimited by virtue of the fact that the wall of the chamber lies directly on the test-field surface along one or more delimitation lines or lies in the vicinity of the test-field surface such that a region of the test-field surface that is not covered by the wall is accessible to the sample, but, by contrast, a region covered by the wall is not. The delimitation line may in the process extend around the whole test-field surface accessible from the chamber such that the delimitation line completely defines the circumference of the test-field surface accessible from the chamber. It is also possible for the wall of the chamber to define merely some of the circumference of the test-field surface accessible from the chamber, with the remaining delimitation of the test-field surface accessible from the chamber for example being brought about by a lateral delimitation of the test-field surface itself, for example by an edge of a test-field surface pressed on a support, which edge is not covered, or only partly covered, by the wall of the chamber.

The test-field surface accessible from the chamber can preferably be entirely defined by the chamber wall such that, for example, the chamber wall entirely defines the test-field surface accessible from the chamber. By way of example, this can be brought about by virtue of the fact that, as illustrated above, one or more openings are provided in the wall of the chamber, which openings are also referred to as "windows" in the following text and can, in principle, have any shape. Rectangular or round shapes of the windows are particularly preferred. Alternatively, the chambers and/or a housing of the analytic magazine may also have an indentation and/or a blind hole, for example in a chamber wall and/or in another part of the housing. In this respect, the term chamber wall should be considered quite broadly and in principle may, in addition to elements that delimit the actual dimensions of the chambers, also comprise other elements of the chambers and/or the housing, which elements can delimit the access to the test field.

By at least partly covering the test field with the wall of the chamber, it is possible in particular to cover particularly threatened regions of the test field such that contamination, which can originate from these regions, can at least largely be prevented. As illustrated above, these regions can, in particular, be cutting edges. Accordingly, the test field can more particularly have at least one cutting edge, wherein the wall of the chamber at least partly covers the cutting edge. In particular, the above-described windows can be embodied such that the cutting edge is not a component of the test-field surface that is accessible from the chamber, wherein, analogously, provision can also be made for a plurality of such test-field surfaces. In other words, the cutting edge in particular can be covered such that it is not accessible from the chamber such that, conversely, e.g. particulate contaminants cannot enter the chamber from this cutting edge, or only with great difficulty, so as to contaminate e.g. further components of the analytic aid, for example at least one lancet, there.

Here, a cutting edge should in general be understood to mean a boundary of the test field, which can for example be produced by a spatially structured pressure method and/or a cutting method. By way of example, the test field can be embodied such that it comprises at least one support on which the at least one test chemical is applied, for example in the form of one or more layers. By way of example, as will be explained in more detail below, the support can be embodied to have e.g. a plastic material and/or a paper material and/or another support material that is suitable for holding the at least one test chemical. However, alternatively, use can also be made of so-called free-standing test-chemical films.

By way of example, the edges of the test field can be produced such that the test chemical is for example applied to the support in an already structured fashion. In this case, the boundaries of the structuring, for example the test fields pressed onto the support, should be subsumed under the term cutting edge. However, it is preferred—and this can be implemented alternatively or in addition thereto—for a delimitation of the test fields to be brought about by an actual cutting process, for example by means of a mechanical cutting procedure with at least one blade and/or cutting wheel or a similar cutting element and/or by a differently embodied cutting procedure, more particularly laser cutting or the like. In particular, in the case of this cutting procedure, the test field of the at least one test chemical can be structured at the same time as the optional support element, and so, for example, the test chemical and the support element can be cut at the same time, for example by means of one of the above-described cutting processes and/or a cutting process in the form of a punching process. Various embodiments are possible.

As a result of the above-described concept of covering the at least one cutting edge, it is possible to realize the above-described advantages in an outstanding fashion. The wall of the chamber may have the at least one opening, which is also referred to as a test-element window and/or simply as a window in the following text and which may provide a limited access to the test field from the interior of the chamber. The wall of the chamber itself, more particularly with the at least one opening, thus acts as the above-described separation element in this preferred embodiment, which separation element allows access to the test field from the chamber and at the same time is able to prevent contamination of the interior of the chamber by the test chemical, more particularly by the particulate components. Thus, the test field, which may be embodied as a chemical field, can be integrated into the housing of the magazine, for example wholly or partly. By way of example, the test field can be held in a recess in the magazine housing, for example in a recess accessible from the outside, which is accessible from the interior of the chamber through the at least one opening. By way of example, the test field can be positioned in the recess such that the cutting edges of the test field, e.g. the edges of the test field, are surrounded by the magazine housing. A connection between the interior of the chamber, for example a connection between a lancet element held in the interior of the chamber, and the test element, more particularly the test field, can then be brought about for example exclusively via the aforementioned opening. The aforementioned opening preferably has a small design, for example with a window area, which delimits the test-field surface accessible from the chamber, of 0.01 mm2-5 mm2, preferably 0.05 mm2-0.5 mm2 and particularly preferably 0.25 mm2. This allows the cutting edges of the test element in particular to be covered by the magazine housing, which cutting edges may, for example, be responsible for a crumbling of the test chemical and hence for a particulate contamination.

As illustrated above, the test element can furthermore comprise in particular at least one lancet, preferably at least one microsampler, wherein the lancet can at least partly be held in the chamber and can be designed to hold a sample of a bodily fluid. The analytic magazine may be designed such that the lancet can transfer the held sample to the test field in at least one position. By way of example, provision can be made for a position in which the lancet and/or a capillary of the microsampler are brought into the vicinity of the test field, for example via the aforementioned test-field window within the chamber, such that a transfer is possible. The transfer can also be brought about, or at least be simplified, by one or more additional transfer elements, for example by means of at least one additional actuator. The actuator can be used to act on e.g. the lancet, e.g. the microsampler, and/or the test field in order to press the lancet on the test field, and/or vice versa, such that the sample is transferred to the test field. Accordingly, the lancet can for example be arranged above or below the aforementioned at least one test-element window, for example with a flat side of the lancet facing the test-element window.

The aforementioned actuator, which brings about and/or simplifies the transfer of the sample from the lancet to the test field, can wholly or partly be a component of the analytic magazine and/or can also, wholly or partly, be a component of an analytic system using the analytic magazine. By way of example, one or more corresponding openings can be provided in the housing of the analytic magazine, which openings allow an intervention by the actuator.

Alternatively, or in addition thereto, further actuators may be provided in the analytic magazine and/or the analytic system. By way of example, the analytic magazine can be embodied such that provision is made for a lancet, which is movably mounted in the chamber. The at least one actuator can be embodied such that it can interact with the lancet by means of one or more coupling elements, which may be provided on the lancet and/or on the actuator. In particular, the magazine can be embodied such that the lancet carries out a sample-taking movement, which may, for example, comprise a movement to the skin surface of a subject, a piercing or puncturing process, a collection process and a return movement away from the skin surface of the subject, and may preferably comprise a re-storing of the lancet, for example in the chamber from which it was taken. By way of example, the at least one coupling element can be embodied such that it brings about, preferably in an automatic fashion, a coupling at the beginning of the sample-taking movement and a decoupling at the end of the sample-taking movement. By way of example, the sample-taking movement can be undertaken on a chamber in an application position of the analytic system. By way of example, the analytic magazine can be embodied such that the lancet describes an arced path during movement in the chamber and/or is subjected to a change in shape. By way of example, this arced path and/or the change in shape of the lancet can bring about coupling to the at least one actuator. By way of example, the lance may comprise at least one coupling element, which couples to or decouples from a corresponding coupling element of the actuator as a result of the arc and/or the change in shape. By way of example, this coupling element can comprise an eyelet and/or a pilot hole of the lancet, more particularly of a flat lancet.

As illustrated above, the magazine can, in particular, be designed such that the lancet can transfer the held sample to the test field in at least one position. By way of example, the actuator can be designed to bring the test field into this position, which can also be described as a transfer position, after the sample-taking movement and/or during the sample-taking movement, more particularly at the end of the sample-taking movement, in a chamber that is in an application position of the analytic system. By way of example, the lancet can be positioned relative to the test field in this transfer position such that the sample can be transferred from the lancet to the test field as a result of a direct contact and/or as a result of spatial proximity. In the process, the analytic magazine is preferably designed such that the lancet is mounted in a storage position within the chamber in a rest state, which storage position differs from the at least one transfer position. Here, a rest state should, in particular, be understood to mean a state in which the at least one analytic aid is not used, for example an unused state in which the analytic aid has not yet been used. By way of example, the analytic aids can be in this storage position in unused chambers. Once the chambers or the analytic aids stored therein have been used, the lancets can then remain in the transfer position or, alternatively, can be returned to the storage position and/or brought into another position, for example again with the aid of the at least one actuator of the analytic system.

In particular, the embodiment in which the storage position is separated from the transfer position affords the possibility of avoiding e.g. the lancet coming into contact with the test field. In particular, the storage position can be embodied such that the lancet does not come into contact with the test field when in this position. This can further reduce abrasion and, as a result thereof, e.g. particle formation.

As an alternative to the above-described option of embodying the separation element such that at least one cutting edge of the test element is covered by at least one wall of the chamber, or in addition thereto, it is also possible to implement the at least one separation element in another fashion. The second implementation described below can be embodied as an alternative to the above-described first implementation, or in addition thereto. In particular, the above-described optional embodiments can also be utilized within the scope of the second embodiment of the separation element described below, even if the remaining features of the first concept of the embodiment of the separation element have not been implemented. Hence, by way of example, the additional features of the dependent claims relating to the first concept can also be implemented, separately from the implementation of the first concept, within the scope of the second concept described below.

As illustrated above, the common basic idea of the present invention consists of providing at least one separation element, which, on the one hand, should allow at least partial access of the sample of the bodily fluid and/or components of the sample of the bodily fluid to the test field but which, on the other hand, should, in the opposite direction, make it more difficult for contaminants, more particularly particulate contaminants, to reach the interior of the chamber, starting from the test element. According to the invention, the second concept proposes to implement this separation element such that it comprises at least one membrane or is formed by at least one membrane.

Accordingly, an analytic magazine is proposed, more particularly as per one or more of the above-described optional embodiments, which comprises at least one chamber with at least one analytic aid, which comprises at least one test element for detecting at least one analyte in a sample of a bodily fluid. The test element comprises at least one test field with at least one test chemical. Reference can largely be made to the above description in respect of possible definitions of the terms, and possible optional embodiments. In particular, the test element can also be arranged wholly or partly within the chamber, i.e. once again be accessible from the chamber. More particularly, the test field can in turn be wholly or partly integrated into a chamber wall, for example by providing at least one opening in the form of at least one test-element window, through which the sample of the bodily fluid can reach the at least one test field.

Within the scope of the second concept, it is proposed to arrange at least one membrane between the test field and an interior space of the chamber. In this case, the aforementioned separation element thus comprises a membrane and/or is formed by such a membrane. The membrane is embodied to be at least partly permeable, i.e. pervious, to the sample, more particularly to blood or blood constituents. However, the membrane is at least partly impermeable to the test chemical, and so ingress of components of the test chemical into the chamber is substantially prevented. A "substantial" prevention should be understood to mean being impermeable to the extent that at least solid chemical components down to the size of bacteria, e.g. components larger than 10 micrometers, are held back.

Here a membrane should be understood to mean an element that allows the passage of the sample and/or components of the sample through this element itself, at least in part, that is to say which is at least partly permeable to the sample and/or components of the sample, more particularly to blood and/or interstitial fluid and/or other bodily fluids. By way of example, the membrane can wholly or partly be embodied as a porous material that is permeable to the sample and/or components of the sample. By way of example, in this case it may be a porous plastic material. By way of example, the porous material can comprise a multiplicity of pores, which for example enable the passage of the sample and/or components of the sample but which hold back components of the test chemical, for example particles of the test chemical. By way of example, the membrane may comprise a hydrophilic material. However, in principle, other embodiments are also possible. At the same time, the membrane is embodied such that it at least substantially holds back the test chemical and/or components of the test chemical, at least in the dry state, more particularly that it holds back possibly toxic elements of the test chemical, and/or elements of the test chemical that may cause allergic reactions, for example enzymes. In particular, the membrane can be embodied to be at least largely impermeable to particulate components of the test chemical, at least in the dry state, preferably to components of the test chemical with particle dimensions and/or a diameter of more than 10 µm. Hence, this may be a semi-permeable membrane that is dimensioned such that it is impermeable to the test chemical in the dry state, more particularly to one or more enzymes contained in the test chemical, but that it is permeable to the liquid sample, more particularly blood, such that a corresponding blood transfer and/or a transfer of other types of samples of bodily fluid can take place from the interior of the chamber to the test chemical, more particularly the test field.

The test field, more particularly a test-field surface of the test field that is accessible from the chamber, is preferably at least partly, preferably wholly, covered by the membrane. The membrane can preferably lie directly on the test field such that no interspace, or preferably an interspace of 5 µm or less is produced between the test field and the membrane. This allows the membrane or, in the moist state, the sample of the bodily fluid held in the membrane itself to act as a reservoir of the bodily fluid for the detection reaction taking place in and/or on the test field.

In particular, the membrane can be embodied as a film or comprise at least one film, i.e. an element whose lateral extents exceed its thickness a number of times, preferably by a factor of 10, more particularly by a factor of 100 or more. The membrane, more particularly the semi-permeable membrane, can furthermore be embodied such that it has a spreading effect in the lateral direction, i.e. in a direction perpendicular to the passage direction of the sample of bodily fluid. Such a spreading effect causes the sample geometry to dilate perpendicular to the passage direction, and so the sample is distributed more evenly on the test field or on the test-field surface that is accessible from the chamber.

As illustrated above, the membrane preferably has a semi-permeable design and is at least partly permeable to bodily fluids, but at least partly impermeable to components of the test chemical, more particular particulate components. In general, the requirements on the membrane are such that it can in particular have a retaining effect for particulate components of the test chemical. In principle, the membrane can, to this end, have e.g. a mean pore dimension, which in particular may be specified as a so-called d50 value, of between 1 µm and 10 µm, preferably of between 2 µm and 5 µm. In particular, the membrane can comprise a pore network wherein the mean pore dimensions, which can be determined in the usual fashion, can satisfy the aforementioned condition. By way of example, in this case a pore dimension can be considered to be a mean diameter and/or a mean equivalent diameter of all individual pores within the membrane. Symmetric membranes with uniform pore distribution throughout, between the two sides and/or over the entire thickness of the membrane, are preferred.

Pores with a pore dimension of 10 µm or less are particularly suited to prevent the ingress of particulate components into the interior of the chambers. Furthermore, such pores are also suitable for preventing typical microbiological contaminants, more particularly bacteria, from entering into the interior of the chambers through the membrane. By way of example, this makes it possible to maintain a sterile protection. On the other hand, the preferred lower bound, according to which the minimum pore dimension is 1 µm or more, ensures that the sample, more particularly an aqueous sample such as e.g. blood and/or interstitial fluid, can at least partly pass through the membrane. In the case of pore dimensions of less than 1 µm, the access of the sample to the test field from the interior of the chamber is at least made significantly more difficult.

As illustrated above, the membrane is preferably embodied as a film membrane. In particular, the membrane can have a thickness, i.e. an extent parallel to the passage direction of the sample of the bodily fluid toward the test field, that preferably lies between 30 µm and 150 µm, more particularly between 50 µm and 100 µm. This preferred thickness not only affects the above-described retaining effect for particulate contaminants and/or microbial contaminants whilst at the same time allowing the sample to pass, the aforementioned preferred thickness of the membrane can also bring about the above-described provision of a liquid reservoir of the sample of the bodily fluid above the test field. Thus, it was found in the case of known test chemicals in particular, more particularly for detecting blood glucose, that a liquid column of at least 30 µm, preferably at least 50 µm above the test field is desirable. Smaller liquid columns, for example smaller blood columns, can make the detection reaction dependent on the actual height of the blood column as a result of diffusion effects. By contrast, in the case of thicknesses of 30 µm or more, preferably 50 µm or more, the reaction, for example a color reaction, for detecting the at least one analyte is, in most cases, largely independent of the actual height of the liquid column. However, on the other hand, the increasing thickness of the membrane has a negative effect on the permeability of the membrane to the liquid sample and on the necessary sample volume, and so the aforementioned upper limits of the thickness of at most 150 µm, more particularly at most 100 µm, should be preferred.

In principle, any organic and/or inorganic materials that satisfy the aforementioned properties can be used for the membrane. These materials can be applied in the form of one or more continuous layers and/or else be in the form of structured materials, for example in the form of materials embodied with loops, for example fabrics and/or knitted fabrics. However, continuous, porous materials are preferred. In particular, the membrane can have hydrophilic properties. More particularly, the membrane can comprise a plastic material, preferably a hydrophilic plastic material, and/or it can be completely produced from such a plastic material. In particular, the membrane material should be a material whose properties substantially remain unchanged when the analytic magazine is sterilized, for example by means of electron beam sterilization and/or gamma-ray sterilization.

The use of one or more of the following materials is particularly preferred: a cellulose and/or a cellulose derivative, more particularly a nitrocellulose; a polysulfone; a nylon; a polyvinylidene fluoride; a regenerated cellulose; a hydrophilic polyurethane. In particular, use can be made of materials that are typically used in filters, for example water filters. As an alternative to materials that inherently have hydrophilic properties, or in addition thereto, less hydrophilic materials are also suitable, which were subsequently hydrophilized, for example by means of a wetting agent. A person skilled in the art is aware of suitable wetting agents.

By way of example, the membrane can be introduced into the analytic magazine by means of one or more membrane bodies. By way of example, the membrane can also be provided for a plurality of chambers at the same time. Thus, by way of example, provision can be made for a membrane body with individual membranes, which are each associated with a chamber. This can make the production of the membrane much simpler.

By way of example, the membrane can have at least one structuring with at least one passage area that has the aforementioned properties in respect of the permeability to the sample and the impermeability to the test chemical and is at least partly permeable to the sample of the bodily fluid, and with at least one impermeable area that is at least partly impermeable to the sample of the bodily fluid. Hence, the passage area forms the actual membrane with the aforementioned properties, i.e. the aforementioned at least one separation element or a part of the latter. By way of example, this passage area can be a region in which a blood transfer from the lancet to the test field can take place within the chambers.

Various methods can be utilized to structure a membrane as mentioned above. Thus, for example, the structuring of the membrane into passage areas and impermeable areas can be brought about by appropriately coating the membrane, in which, for example, the impermeable areas are provided with an impermeable coating. However, alternatively, or in addition thereto, the structuring can also for example be brought about by thermal methods, for example by the targeted closure of the membrane pores and/or other openings in the membrane in the impermeable areas, for example by introducing sealant materials such as adhesives and/or by fusing the membrane material. By way of example, this can be brought about by laser structuring, within the scope of which, for example, the material of the membrane is at least partly fused in the impermeable areas such that the impermeable property is produced.

If provision is made for a plurality of chambers, at least one passage area can for example be provided in each case for each chamber. This at least one passage area can for example correspond to the above-described openings in the chamber wall and/or completely close these openings or be introduced into these openings. By way of example, in terms of their geometry, the passage areas can be matched to correspond to the aforementioned openings, more particularly the test-element windows, or they can for example be embodied to be slightly larger than these openings and can be arranged corresponding to these openings and/or for example wholly or partly cover these openings.

The membrane can also, at the same time, be embodied for a number of chambers. By way of example, the membrane can have a common form for all chambers and can in each case provide at least one passage area for the number of chambers, more particularly for all chambers. By way of example, the membrane can comprise a common membrane body for all chambers, with respectively at least one passage area for each chamber. By way of example, the common membrane body can comprise a membrane ring and can for example be introduced into a recess of the housing of the magazine or can be connected to the housing of the magazine in a different fashion and/or integrated into this housing.

By way of example, as explained above, the analytic magazine can comprise a housing. This housing may also consist of a plurality of housing parts. The test element can be wholly or partly integrated into the housing. The housing can have at least one opening facing the at least one chamber, for example the above-described test-field windows, preferably at least one opening per chamber. By way of example, the membrane can be applied to the opening from the outside and can be accessible from the chamber through the opening, which was referred to as a window above. The test field is preferably applied to the membrane from the outside such that, for example, as seen from the chamber or the interior of the chamber, the membrane is firstly arranged through the opening, followed by the at least one test field.

In particular, the membrane can be connected to the housing. In principle, this connection can be brought about by any type of connection, which can also be combined. Interlocking connections are particularly preferred. The at least one connection particularly preferably comprises a welded joint and/or a connection produced by heat staking. Laser welded connections are particularly preferred in this context because of the low tremors during welding. However, alternatively, or in addition thereto, use can also be made of thermal welded joints and/or ultrasound welded joints and/or other types of welded joints. As an alternative to the welded joints, or in addition thereto, use can, for example, also be made of adhesive connections, i.e. connections in which the membrane is wholly or partly bonded onto the housing. By way of example, this can be brought about by virtue of the fact that in each case at least one passage area is positioned in front of at least one opening of the housing.

In order to hold the at least one membrane, the housing or at least one housing part of the housing can comprise elements that ease the connection between the membrane and the housing and/or a positioning of the membrane relative to the housing. By way of example, provision can be made for corresponding holding elements, such as recesses, grooves, hooks, eyelets, projections or the like, or combinations of the aforementioned and/or other elements. By way of example, as explained above, the membrane can be embodied in the form of a membrane ring, which can, for example, be introduced into a corresponding radial groove in the housing.

As illustrated above, it is also possible for the at least one test field to be wholly or partly integrated into the housing. Thus, the test field can for example be connected to the housing and/or at least one housing part and hence itself become a component of the housing. In principle, the test field can in turn be connected to the housing in different ways. In general, force-fit and/or interlocking connections are particularly preferred, particularly clip-on connections.

By way of example, a test field can be applied to the housing from the outside by means of such a connection, for example it can be clipped on. This application is preferably brought about by virtue of the fact that the above-described optional openings, optionally with the introduced and/or overlying membrane, are wholly or partly covered.

The force-fit and/or interlocking connection can for example be made simpler by one or more connection elements that can be provided on the housing and/or on at least one housing part. Thus, by way of example, corresponding latch-connection elements and/or other types of connection elements, for example, grooves, projections, hooks, or the like, or combinations of the aforementioned and/or other connection elements, can be provided on the housing. By way of example, the test field in the form of a chemical ring and/or a chemical disk can be clipped onto the housing from the outside.

A substantial advantage of the analytic magazine according to the invention consists of the fact that the test field can also be connected to the housing independently in terms of time and/or independently in terms of procedure from the at least one membrane being connected to the housing. This affords the possibility of producing sterile semi-finished products of the analytic magazine, which semi-finished products can optionally be sterilized and/or temporarily stored in order subsequently to apply the test fields. Thus, for example, use can be made of a production method for the analytic magazine, in which the membrane is firstly connected to the housing and/or at least one housing part of the analytic magazine. This is preferably brought about by virtue of the fact that the at least one chamber is sealed by the at least one membrane such that preferably no particulate contaminants and/or microbial contaminants, more particularly no bacteria, are still able to enter the interior of the chamber, at least through the at least one membrane.

Further analytic aids and/or partial aids, such as e.g. one or more lancets, can be introduced into the at least one chamber prior to or after the above. As a result of this, the lancets can be protected by the membrane, more particularly they can be stored in a sterile fashion. After the at least one membrane is connected to the housing, it is then optionally possible to sterilize the partly completed magazine, for example by undertaking a sterilization by gamma rays and/or a sterilization by electron beams. The magazines thus partly completed can then, for example, be stored temporarily and can optionally provide a common platform for very different types of analytic magazines, for example with different test chemicals. In a further method step, which can also be done at a later stage, the at least one test field can then be connected to the housing, for example by means of one or more of the connection types described above. In principle, in accordance with the aforementioned platform idea, any type of test chemical can be selected in the process. Thus, for example, a batch of analytic magazines can be defined as late as in this method step, in accordance with, for example, the applied at least one test chemical.

Furthermore, a method for producing an analytic magazine is also proposed in addition to the analytic magazine in one or more of the above-described embodiments. In particular, the method can be used to produce an analytic magazine according to one or more of the above-described embodiments such that, in respect of possible embodiments of the method, reference can be made to the above-described possible embodiments of the analytic magazine. The method can accordingly be complemented by one or more method steps in which the preferred options are implemented. The analytic magazine comprises at least one chamber with at least one analytic aid. The analytic aid comprises at least one test element for detecting at least one analyte in a sample of a bodily fluid. The test element comprises at least one test field with at least one test chemical. At least one lancet element, for example a microsampler, is introduced into the chamber within the scope of the method.

The method furthermore has the following method steps, which are preferably, but not necessarily, carried out in the illustrated sequence. Individual method steps or a number of method steps can also be carried out overlapping in time and/or at the same time and/or repeatedly. Furthermore, the method can comprise additional method steps that are not listed in the following. The method comprises the following steps:

at least one housing part of a housing of the analytic magazine is produced;
the test field is produced; and
the test field and/or the test element is connected to the housing part such that the test field is at least partly accessible from the chamber for placing a sample, wherein at least one wall of the chamber at least partly covers the test field and thereby at least partly delimits a test-field surface that is accessible from the chamber.

In particular, the method can be carried out such that the test element and/or the test field are produced using a cutting method. In particular, the wall of the chamber can, as described above, cover at least one cutting edge of the test field.

By way of example, at least one membrane can be introduced in a further method step as a further method step, more particularly before the test field and/or the test element is connected to the housing part, for example by likewise connecting said membrane to the housing part. Reference can for example be made to the description above in respect of further embodiments, particularly in respect of the embodiment and/or arrangement of the membrane.

By way of example, the membrane can firstly be connected to the housing and/or the at least one housing part such that a semi-finished product can be created. This semi-finished product can for example comprise all parts of the analytic magazine except for the test element and/or the test field. By way of example, the semi-finished product can be sterilized and/or temporarily stored. The semi-finished product can then be complemented at a later date by the described method step of attaching the test element and/or the test field to form the analytic magazine.

The test field and/or the test element can be connected to the housing part at a time at which the housing has almost been completed (i.e. in particular completed bar the test element), or at a different time. Thus, by way of example, provision can be made for a plurality of housing parts, which are assembled. In this case, the test element and/or test field can be connected to the at least one housing part before, during, or after the assembly of the housing parts. More particularly, the at least one chamber does not necessarily have to be fully completed when the test element and/or test field is connected to the housing part, but use can, for example, also be made of a method in which the chamber is only completed at a later time, for example after further housing parts have been introduced. Furthermore, the cover of the test field provided by the chamber wall, by means of which a test-field surface accessible from the chamber is delimited, does not necessarily have to be produced by the housing part to which the test element and/or the test field is connected; rather the wall can, additionally or alternatively, also at least in part be formed from one or more of the other housing parts.

The analytic magazine as per one or more of the above-described embodiments and the proposed method has a number of advantages over known analytic magazines, more particularly integrated analytic magazines with at least one lancet and at least one test element, and over known production processes. Thus, a contamination of lancets in the chambers of the analytic magazines, in particular by microbial contaminants and/or particulate contaminants, can be effectively prevented. However, at the same time a high system integration can be implemented because test elements and lancets can be held together within the chambers.

Furthermore, the analytic magazines can be implemented comparatively easily from a technical point of view because the aforementioned separation elements can be provided in few production steps and using fewer individual parts in order to produce the analytic magazines. In particular, magazines with a dry assembly of the at least one membrane over or under a separately designed test field can be implemented in a simple fashion.

DRAWINGS

Further details and features of the invention emerge from the following description of preferred exemplary embodiments. Here, the respective features can be implemented individually or together in combination. The invention is not restricted to the exemplary embodiments. The exemplary embodiments are illustrated schematically in the figures; here, the same reference signs in the individual figures denote identical or functionally identical elements, or elements that correspond in respect of their function.

FIGS. 4A and 4B show a further exemplary embodiment of a chamber according to the invention of an analytic magazine with a lancet in various positions.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

Figure 1:
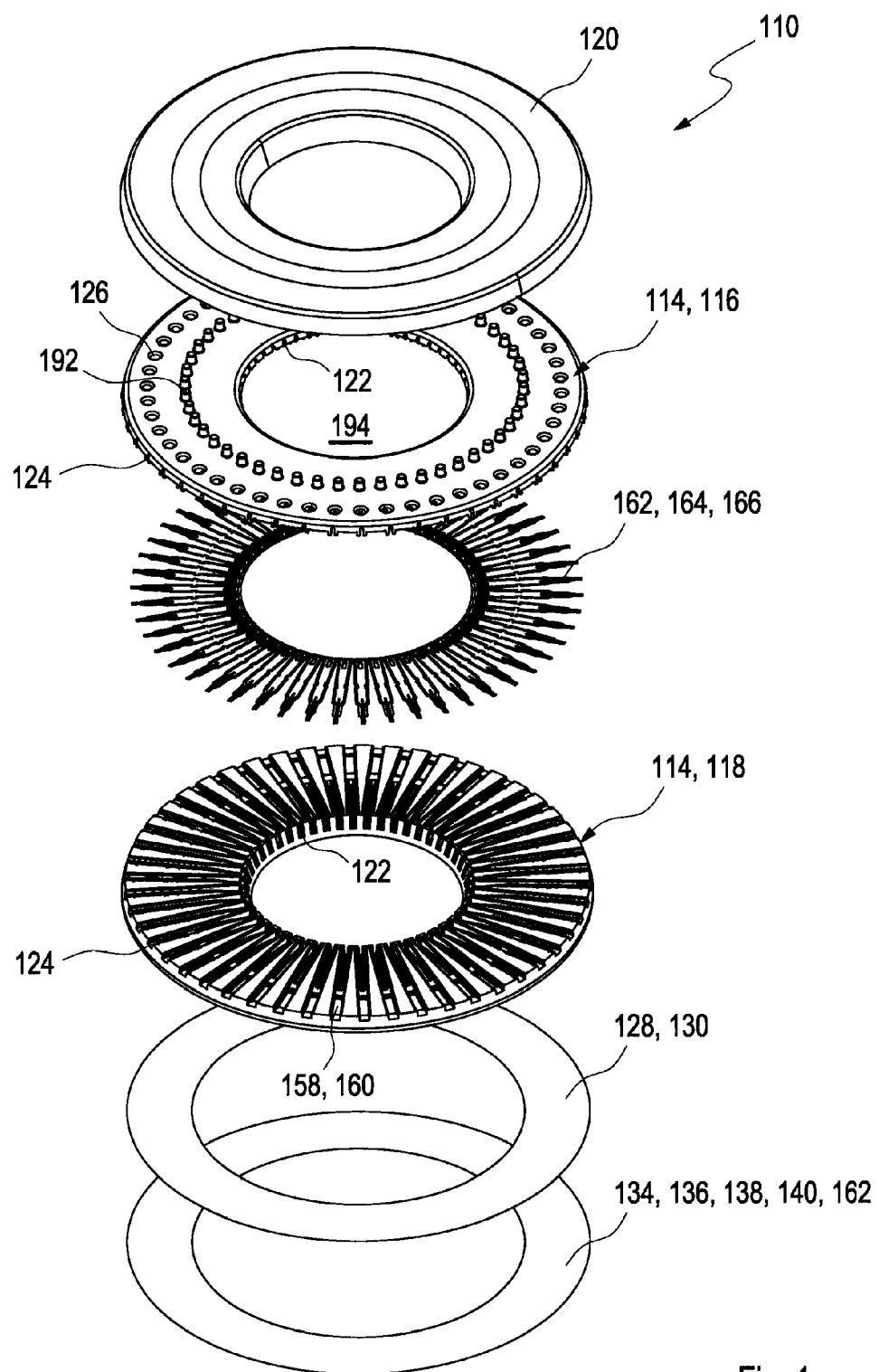
FIG. 1 shows an exploded view of an exemplary embodiment of an analytic magazine.
Figure 2:
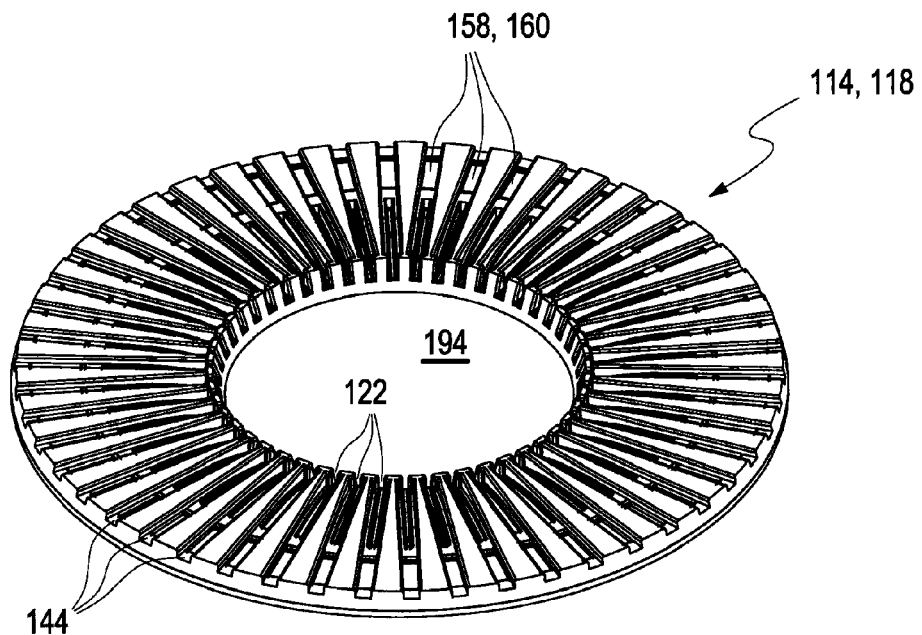
FIGS. 2A to 2E show various individual parts of the analytic magazine as per FIG. 1.
Figure 2:
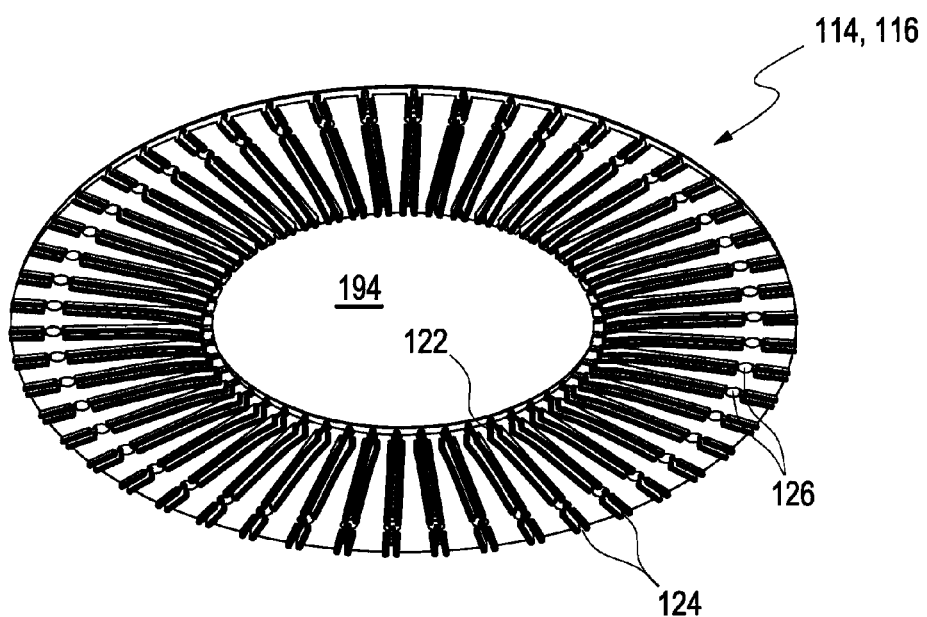
Figure 2:
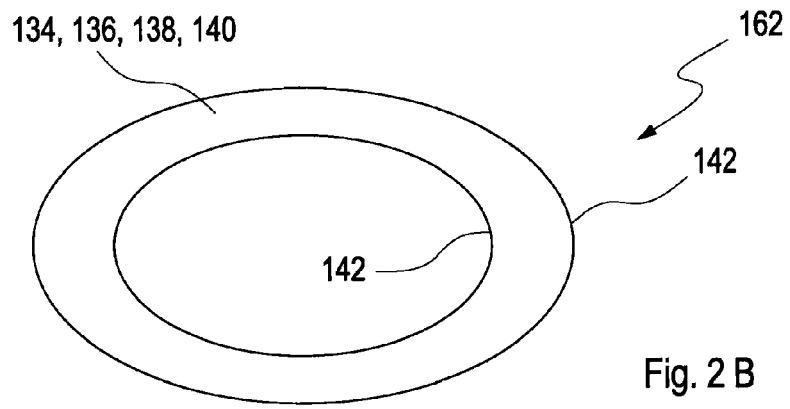
Figure 2:
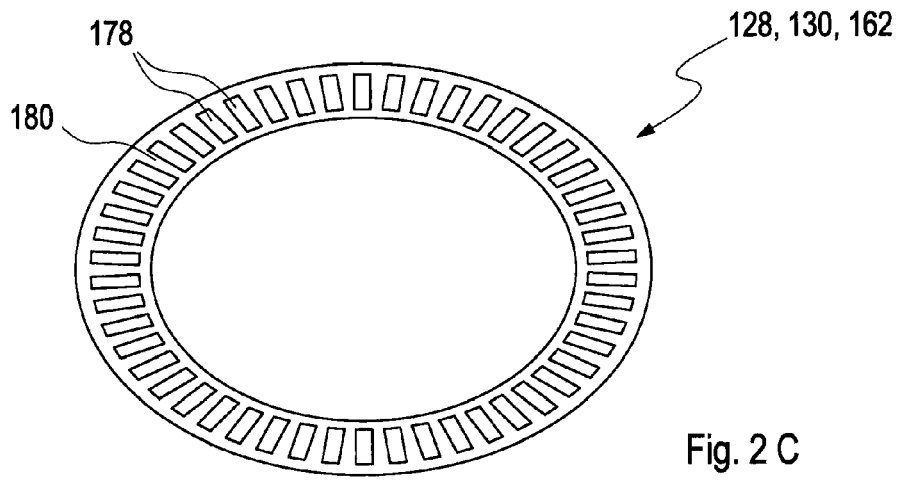
Figure 2:
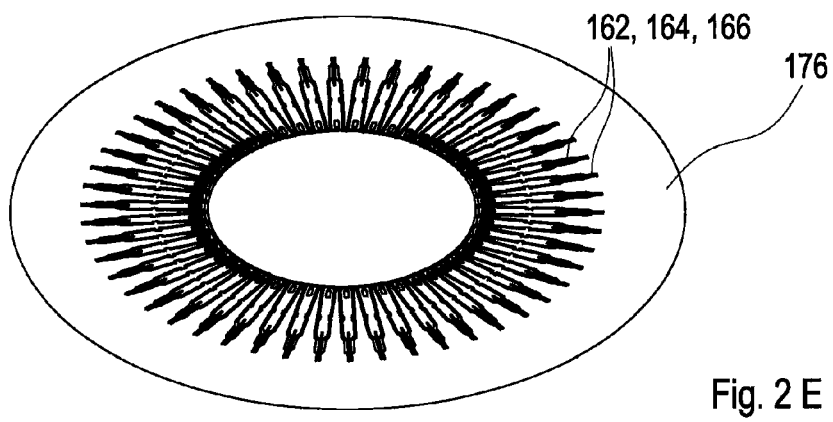
Figure 3:
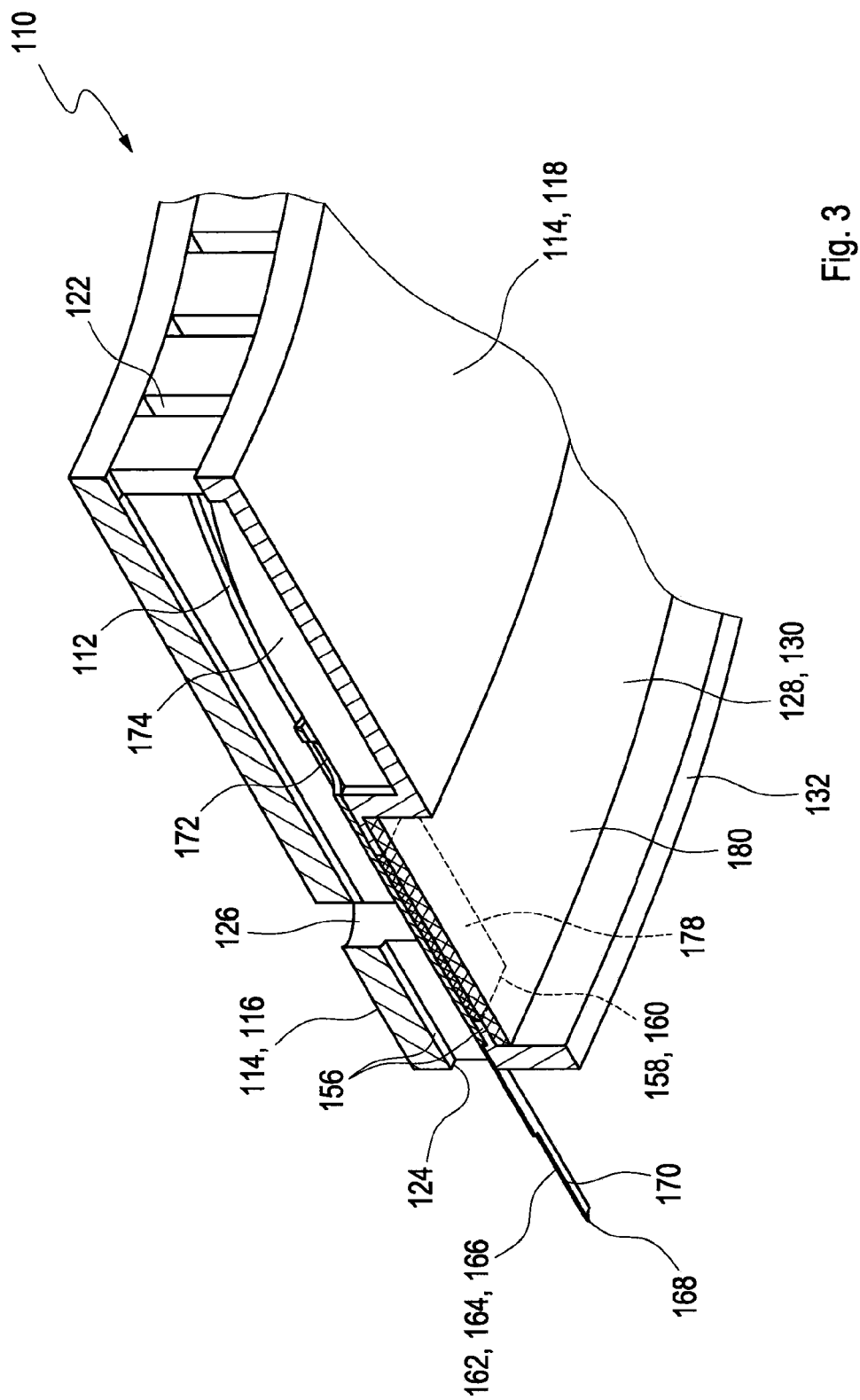
FIG. 3 shows a perspective sectional view through a chamber of the analytic magazine as per FIG. 1.

FIGS. 1 to 3 illustrate a first exemplary embodiment of an analytic magazine 110 according to the invention. In the following text, these figures are described collectively. By way of example, the analytic magazine 110 can be used in an analytic system (not illustrated in the figures). FIG. 1 shows an exploded view of the analytic magazine 110, whereas FIGS. 2A to 2E show some components of the analytic magazine 110. FIG. 3 shows a perspective sectional view through a chamber 112 of the analytic magazine 110.

The analytic magazine 110 comprises a housing, which has a multi-part design and which is denoted by reference sign 114 in FIG. 1. This housing 114 comprises a first housing part in the form of an upper shell 116 and a second housing part in the form of a lower shell 118. The lower shell 118 is once again shown in FIG. 2A, in a perspective illustration obliquely from above, whereas the upper shell 116 is once again shown in FIG. 2D, in a perspective illustration obliquely from below.

The analytic magazine 110 furthermore comprises one or more optional seals 120, which can merely be identified in the perspective illustration as per FIG. 1 and which can for example be used to seal internal openings 122 and/or external openings 124 and/or actuator openings 126 (see FIGS. 4A, 4B, and 3 in particular). By way of example, the seal 120 can comprise a plastic film and/or a metallic film, which can for example be shaped in a deep-drawing method and onto which the openings 122, 124, and/or 126 can be applied, for example by laminating or ironing them on.

The analytic magazine 110 furthermore comprises a membrane 128 in the form of a membrane ring 130 below the lower shell 118, which membrane can be integrated into the housing 114 and hence can form part of the housing 114. This membrane ring 130 can be introduced into an annular groove 132 on the underside of the lower shell 118 and can optionally be connected to the lower shell 118 by means of a welding process, for example. The membrane ring 130 is shown in a plan view in FIG. 2C and will be explained in more detail below.

The analytic magazine 110 furthermore comprises test elements 134, which, in this exemplary embodiment, are represented as a test field 136, common to all chambers 112, in the form of a test chemical ring 138. By way of example, this test chemical ring 138 can comprise a test chemical 140 on its side facing the lower shell 118, more particularly a substantially moisture-stable test chemical, for example as per the type shown in WO 2007/012494 A1 (see also, US 2008/0213809).

In principle, other types of test chemicals are also feasible. By way of example, the test chemical ring 134 can furthermore comprise one or more support elements, for example likewise in the form of rings, such that the actual test chemical 140 and the support can for example be embodied as a ring in a congruent fashion. The test chemical ring 138 respectively has cutting edges 142 on its inner circumference and on its outer circumference. The test chemical ring, which is not illustrated in FIG. 3, can, for example, likewise be introduced into the annular groove 132 on the underside of the lower shell 118. By way of example, the test chemical ring 138 can be connected to the lower shell 118 by one or more connection elements, for example by clip-on connections. These connection elements, which can also be formed on the lower shell 118, are likewise not shown in FIG. 3.

The chambers 112 are formed by recesses 144 in the upper shell 116 or in the lower shell 118, which respectively correspond to one another and which form walls 156 of the chambers 112 when the upper shell 116 and lower shell 118 are assembled.

Furthermore, openings 158, which face the annular groove 132, are formed in the lower shell 118, which openings act as test-element windows 160. These openings 158, indicated in one case in FIG. 3 by a dashed line, have a rectangular design, wherein respectively one opening 158 is associated with one chamber 112 in the illustrated example. The openings 158 are completely covered by the membrane ring 130; this likewise emerges from FIG. 3. Hence, it is only restricted test-field surfaces of the entire test field 136 that are accessible through the openings 158 from the interior of the chamber 112. Hence, these test-field surfaces are substantially defined by the opening 158. If the test chemical ring 138 is inserted into the annular groove 132, the edges of the openings 158 and hence the walls 156 of the chambers 112 cover the cutting edges 142 of the test chemical ring 138 such that these are not accessible from the interior of the chambers 112.

The test field 136 or the test-field surfaces of the test field 136 respectively accessible from the chambers 112 are components of analytic aids 162 arranged in the chambers 112. Furthermore, these analytic aids 162 comprise lancets 164 in the form of so-called microsamplers 166. In addition to a lancet tip 168, these microsamplers 166 comprise capillary gaps 170, respectively leading away from the lancet tip 168, which capillary gaps can be identified in the perspective illustration as per FIG. 3 in particular and which are designed to hold a sample of a bodily fluid, more particularly blood, when the skin of a subject is punctured.

At their rear end facing the internal openings 122, the microsamplers 166 furthermore comprise coupling elements 172, which are embodied in the form of eyelets and/or pilot holes in the illustrated exemplary embodiment. An actuator (not illustrated in the figures) of an analytic system can penetrate into the chambers 112 through the internal openings 122 and an actuator groove 174, which can be a component of the recesses 144 in the lower shell 118 and/or the upper shell 116, wherein, for example, the seal 120 can be perforated at the internal openings 122. The actuator can likewise comprise coupling elements, for example hooks that can engage into the coupling elements 172 of the lancets 164. The lancets 164 are movably mounted on an arced path in the chambers 112; this emerges from FIG. 3. If the lancets 164 are arranged in the vicinity of the internal openings 122 with their rear end, the coupling element 172 of each lancet is bent away from the hook of the actuators and decoupled. By contrast, if the lancets 164 are displaced forward, toward the external opening 124, the lancet is stretched due to the shaping of the cavity of the chambers 112, the coupling elements 172 move upwards and latch into the corresponding hooks of the actuators.

A test by means of an analytic aid 162, for example whilst using an appropriate analytic system, can, in particular, be carried out as follows: first of all, an actuator rod enters the interior space of a chamber 112 through an internal opening 122 when the system is in an application position and said rod couples to the coupling element 172 of the lancet 164. The lancet 164 is driven forward, perforates the seal 120 at the external opening 124 and carries out a sample-taking movement. In the process, the lancet tip 168 is driven into the skin of a subject, generates an opening in the skin of the subject and thereby provides a sample of a bodily fluid, for example a blood sample and/or a sample of interstitial fluid. The sample is held by the lancet 164, more particularly the capillary gap 170 of the microsampler 166. Subsequently, there can be a return movement of the lancet 164 into the chamber 112, during which the lancet 164 can also be stored again; this is also part of the sample-taking movement. An actuator bolt of the system can subsequently penetrate into the interior of the chamber 112, from the direction of the upper shell 116 and through the corresponding actuator opening 126, and can press the microsampler 166 onto the test field 136 such that the sample is transferred onto the test field 136. Alternatively, or in addition thereto, pressure can also be exerted on the test field 136 so that the latter approaches the lancet 164 and thereby ensures the transfer. Other transfer mechanisms, as described in more detail below on the basis of FIGS. 4A and 4B, are also feasible. When an actuator penetrates the actuator opening 126, it is likewise possible for the seal 122 on the upper shell 116 to be perforated in turn.

After the sample has been transferred to the test field 136, there may for example be a change in color, which originates from the underside of the analytic magazine 110, in the test field 136 in the region of the opening 158, for example by means of appropriate optical detectors, illuminations or similar elements known to a person skilled in the art.

Following the analysis, before the latter, or at the same time as the analysis, there can in turn be a decoupling of the actuator rod from the coupling element 172, for example by withdrawing the lancet 164 back into the chamber 112 to the extent that the coupling element 172 bends out of the lancet plane of the lancet 164 and is thus released from the hook of the actuator rod. The actuator rod can then leave the chamber 112 again through the internal opening 122.

The assembly illustration of the analytic magazine 110 shown in FIG. 1 allows identification of the fact that the shown analytic magazine 110 comprises 50 analytic aids 162 in the illustrated example. As can be identified from e.g. FIG. 2E, the lancets can for example be etched out of a common metal disk 176, and can still be connected to this metal disk 176 by means of e.g. webs or other connection elements. Accordingly, the lancets 164 can be collectively inserted into the recesses 144 in the lower shell 118. The lancets 164 can subsequently be broken out of the metal disk 176, either simultaneously or in succession, by an appropriate procedure such that the lancets 164 can in general be inserted into the individual chambers 112 at the same time.

The membrane 128, which has been embodied as a membrane ring 130 for all chambers 112 simultaneously in the illustrated embodiment, can substantially have a homogeneous design and can respectively provide at least one passage area 178 for a number of chambers or, as illustrated in the figures, for all chambers, through which passage area a liquid sample from the interior of the chamber 112 can reach the associated test-field surface of the test field 136. However, as likewise indicated in FIGS. 2C and 3, the membrane 128 can also have a structured design and can comprise areas 180, which are impermeable to the sample of the bodily fluid, in addition to the passage areas 178, which can, for example, substantially correspond to the openings 158 of the test-element windows 160.

Hence, in the exemplary embodiment illustrated in FIGS. 1 to 3, the analytic magazine 110 is embodied as a disk-shaped magazine in the form of a circular disk and contains 50 analytic aids 162 in this exemplary embodiment. The production is cost-effective and generally does not require a biocompatible test chemical 140, or has significantly lower requirements in respect of biocompatibility of the test chemical 140, because the membrane 128 can prevent a test chemical 140 from penetrating into the interior of the chamber 112. Hence, the membrane 128 can have a substantially semi-permeable design and can be placed between the lower shell 118 and the chemical ring 138. In particular, the membrane 128 can have a porous design with pores that are so small that they are germ-tight and substantially do not allow to pass chemical dust from the test chemical 140. On the other hand, it lets e.g. blood, components of the liquid, e.g. plasma and glucose, pass when wetted with a liquid.

Hence, the interior space of the chambers 112 is protected twice against contaminants by particulate contamination and germs. On the one hand, the edges of the openings 158 in the walls 156 cover the cutting edges 142 of the test chemical ring 138, which is particularly prone to particles. On the other hand, the membrane 128 provides further protection of the interior space of the chamber 112 against germs and chemical dust.

During production, the membrane ring 130 can firstly for example be introduced into the annular groove 132 in the lower shell 118, for example after connecting the upper shell 116 and the lower shell 118, for example by means of a laser welding method, and, optionally, after applying the seal 120, and said membrane ring can be connected to the lower shell 118, for example to webs of this lower shell 118, by means of heat staking or similar connection techniques. The structuring indicated in FIG. 2C can occur concurrently with this connection. Alternatively, or in addition thereto, the indicated structuring into passage areas 178 and impermeable areas 180 can also take place separately; however, this requires a positioning of the membrane ring 130 relative to the openings 158. Away from the individual fields of the passage areas 178, the membrane 128 can be compacted, for example as a result of thermal action, such that the impermeable area 180 is created in the form of a compacted film, which for example no longer takes up liquid. A local laser treatment can also, for example, compress the structure to form a film. It is merely in the uncompressed fields of the passage areas 178 that the membrane function thereof is still maintained. By way of example, a field dimension of the passage areas 178 can for example be approximately 0.5 mm×0.5 mm.

The remaining components can then be connected after the membrane ring 130 has been introduced, provided this has not already taken place, and, for example, it is possible to assemble and optionally connect the lower shell 118 in the form of a base wheel, the microsampler 166, and the upper shell 116 in the form of a cover wheel.

A semi-finished product produced thus can then, for example, be sterilized and can subsequently be stored. In the process, the membrane 128 obtains the sterility of the interior space of the chambers 112. For completion, the semi-finished product then merely needs to be equipped with the test chemical 140. To this end, the test chemical ring 138 can be clipped into the annular groove 132. For this purpose, holding lugs and/or other connection elements, e.g. a projecting ring, can be arranged on the edge of the annular groove 132, for example. The test chemical ring 138 then lies preferably flat and more particularly directly on the membrane ring 130.

In addition to the aforementioned functions, the membrane 128 can fulfill additional functions. Thus, it can for example satisfy a spreading function. Thus, the membrane 128 can for example be designed not only simply to route the sample of the bodily fluid, for example the blood, vertically to the test field 136 but also to spread it onto the entire partial-test-field, for example defined by the associated opening 158, or onto the test-field surface of the test field 136 that is associated with the chamber 112. Hence the wetted field is likewise widened on the test field 136, and the evaluation becomes possible with a simpler optical system. Then, either use can be made of an optical system with a lower resolution or use can alternatively, or in addition thereto, also be made of a miniaturized optical waveguide and/or a conventional optical system, wherein the latter can preferably be routed carefully along wheel structures so that they are able to measure precisely the relevant regions.

As a result of the spread of the sample, the capillary gap 170 or another type of capillary should be filled to a length that is greater than the length of the region of the test field 136, which is defined by the opening 158 and/or the passage area 178, i.e. the test-field surface that faces the chamber 112 or is accessible from the chamber 112. By way of example, if the capillary gap 170 has a length of 2 mm, a lateral spread by approximately a factor of 4 can be obtained in the case of a membrane field in the form of a passage area 178 with a length of 0.5 mm because the membrane 128 takes up the liquid from the capillary gap 170 as a result of suction. These specifications hold true under the assumption that the capillary gap 170 and the membrane 128 have a substantially equal blood-filling level, which is substantially satisfied in the case of a channel depth of approximately 80 µm in the capillary gap 170 and a membrane thickness of, for example, approximately 100 µm. Thus, a wetted field of approximately 0.5 mm×0.5 mm can for example be generated on the test field 136.

Hence, in the exemplary embodiment of the analytic magazine 110 illustrated in FIGS. 1 to 3, there is, as described above, a transfer of a sample of the bodily fluid from the microsampler 166 to the test field 136 by means of separate actuator step, in which part of the actuator penetrates into the interior of the chamber 112 through the actuator opening 126 and moves the microsampler 166 toward the test field 136. Other mechanisms are also possible. A further exemplary embodiment of an analytic magazine 110 is shown in FIGS. 4A and 4B; it implements a different mechanism for transferring a sample 182 of a bodily fluid held by a microsampler 166 to the test field 136. Here, FIGS. 4A and 4B respectively show sectional illustrations from the side through a chamber 112 of an analytic magazine 112, which can otherwise for example be embodied in a substantially analogous fashion to the exemplary embodiment in FIGS. 1 to 3.

Firstly, it is possible to identify the fact that openings 158 are once again formed at the base of the chambers 112 (in the lower shell 118), which openings again are, for example, rectangular test-element windows 160. These openings 158 once again define accessible test-field surfaces, which are denoted by the reference sign 184 in this case, on the test field 136 in the form of the test chemical ring 138. Hence, these accessible test-field surfaces 184 form parts of the analytic aid 162 because these act like individual test fields, analogously to the embodiments in FIGS. 1 to 3. Here, the walls 156 of the chambers 112 once again cover the cutting edges 142 of the test chemical ring 138, and so reference can once again be made to a large extent to the description above.

Moreover, a membrane 128 in the form of a membrane ring 130, also introduced between the test field 136 and the interior space of the chambers 112 in FIGS. 4A and 4B, once again has passage areas 178 and impermeable areas 180, analogously to the exemplary embodiment above. The impermeable areas 180 can once again be produced when the membrane 128 is connected to the lower shell 118 and/or in a separate step, for example by a corresponding compression, and/or in a separate step. As an alternative to a definition by the edges of the openings 158, the accessible test-field surface 184 for each chamber 112 hence can also be defined by the passage areas 178, which can also have a deviating design from the openings 158; for example, they can be larger or smaller.

A mechanism is proposed in FIGS. 4A and 4B for transferring the sample 182 to the test field 136, in which the microsampler 166 lies on the membrane 128 in at least one position. In the case of test elements 134 without a membrane 128, such a mechanism is not recommendable because such lying on the membrane can lead to mechanical abrasion and to a direct transfer onto the microsampler 166 of components of the test chemical 140 that may trigger allergies. However, this can be excluded with almost certainty by the embodiment according to the invention with the membrane 128 because the membrane 128 holds back corresponding particles.

The microsampler 166 is merely indicated in the figures. Here, an unused chamber 112 is illustrated in FIG. 4A, in which the microsampler 166 is, for example, arranged in a storage position 186. The seals 120 on the openings 122, 124 are still intact in this state. By contrast, FIG. 4B shows a situation in which the above-described sample-taking movement has been carried out and in which the microsampler 166 is once again stored in the chamber 112. The interior space of the chamber 112 has such an arced design that the microsampler 166 with the lancet tip 168 describes an arced path. If the microsampler 166 is withdrawn, for example by an actuator of the system (denoted in FIG. 4B by the arrows 190), the lancet tip 168 comes to rest on the membrane 128 in at least one transfer position, denoted by the reference sign 188 in FIG. 4B. After the puncture, the filled lancet 164 can then lie on the membrane 128, for example in an automated fashion, such that this membrane 128 can suction up the liquid sample 182. In this case, there is no need to bridge a gap between the microsampler 166 by the pressure of an actuator, for example a plunger, on the lancet 164; this is analogous to the exemplary embodiment in FIGS. 1 to 3. Hence, an actuator of the analytic system can have a significantly simpler design, and a seal 120 of the actuator openings 126 together with the actuator openings 126 themselves can be dispensed with.

Alternatively, or in addition thereto, it is possible to increase further the contact between the test field 136 and the membrane 128 and/or the microsampler 166, for example by lowering the pressure on the test field 136 from below. Hence, the entire disk of the analytic magazine 110 can be lowered, for example in a last part of the withdrawal 190 of the microsampler 166, and can be pressed with the chemical ring 138 onto an optical system or a similar pressure element.

If the lancet 164 and, more particularly the capillary gap 170 should be prevented from lying on the membrane 128 during a relatively long storage time, for example to avoid damage to the membrane 128 by the lancer 164 and/or to avoid a contamination of the lancet 164 by the membrane 128, provision can optionally be made for the storage position 186, as shown in FIG. 4A. By way of example, this storage position can be embodied such that the lancet 164 is placed slightly further outward in this position, where said lancet lies, slightly raised and, for example, slightly bent, on the edge of the lower shell 118. After the puncture, i.e. after the sample-taking movement, the lancet 164 can then be pulled back slightly further, as indicated in FIG. 4B; the pre-bend relaxes and the microsampler 166 with the filled capillary gap 170 can touch the membrane 128. This can also avoid the lowering of the disk, which was described above as an option, and it can be wholly or partly replaced by the deflection of the lancet 164. Reference is made to the fact that the lancet 164 is merely indicated schematically in FIGS. 4A and 4B and that it may comprise additional elements, for example a lancet shaft, for example analogously to the illustration in FIG. 3.

In general terms, reference is made to the fact that the analytic magazine 110 may comprise a number of additional elements (not illustrated in the figures). By way of example, as indicated on the upper shell 116 in FIG. 1, provision can be made for transport and positioning elements 192, which for example allow a transport mechanism, which is arranged in an internal opening 194 of the analytic magazine, in each case to position precisely one chamber 112 in an application position of an analytic system.

LIST OF REFERENCE NUMERALS

110 Analytic magazine
112 Chamber
114 Housing
116 Upper shell
118 Lower shell
120 Seal
122 Internal openings
124 External openings
126 Actuator openings
128 Membrane
130 Membrane ring
132 Annular groove
134 Test elements
136 Test field
138 Test chemical ring
140 Test chemical
142 Cutting edges
144 Recesses
156 Walls of the chambers
158 Openings
160 Test-element window
162 Analytic aid
164 Lancet
166 Microsampler
168 Lancet tip
170 Capillary gaps 172 Coupling elements
174 Actuator groove
176 Metal disk
178 Passage area
180 Impermeable area
182 Sample
184 Accessible test-field surfaces
186 Storage position
188 Transfer position
190 Withdrawal
192 Transport- and positioning elements
194 Internal opening

What is claimed is:

1. An analytic magazine, comprising at least one chamber with at least one analytic aid, wherein the analytic aid has at least one lancet, wherein the analytic aid furthermore comprises at least one test element for detecting at least one analyte in a sample of a bodily fluid, wherein the test element comprises at least one test field with at least one test chemical, wherein the test field is partly arranged within the chamber and is accessible for the sample of at least one of the bodily fluid and components of the sample from the chamber, wherein at least one wall of the chamber partly covers the test field and thereby delimits a test-field surface of the at least one test field having the at least one test chemical for placing the sample, which test-field surface is accessible from the chamber, wherein the test-field surface is delimited by virtue of the fact that the wall of the chamber lies directly on the test-field surface along one or more delimitation lines or lies in the vicinity of the test-field surface such that a region of the test-field surface that is not covered by the wall is accessible to the sample, but, by contrast, a region covered by the wall is not.

2. The analytic magazine according to claim 1, wherein the test field has at least one cutting edge, wherein the wall of the chamber at least partly covers the cutting edge.

3. The analytic magazine according to claim 1, wherein the wall of the chamber has at least one opening which provides limited access to the test field from the interior of the chamber.

4. The analytic magazine according to claim 1, wherein the lancet is at least partly held in the chamber, wherein the lancet is operable to hold a sample of a bodily fluid, wherein the analytic magazine is designed such that the lancet can transfer the held sample to the test field in at least one position.

5. The analytic magazine according to claim 4, wherein the lancet is movably mounted in the chamber, wherein the lancet describes an arced path during movement in the chamber, is subjected to a change in shape, or both.

6. The analytic magazine according to claim 4, wherein the lancet is mounted in a storage position within the chamber in a rest state, which storage position differs from the at least one position in which the held sample can be transferred to the test field.

7. An analytic magazine, comprising at least one chamber with at least one analytic aid, wherein the analytic aid comprises at least one test element for detecting at least one analyte in a sample of a bodily fluid, wherein the test element comprises at least one test field with at least one test chemical, wherein at least one membrane is arranged between the test field and an interior space of the chamber, wherein the membrane is at least partly permeable to the sample, wherein the membrane furthermore is at least partly impermeable to the test chemical such that an ingress of components of the test chemical into the chamber is substantially prevented, wherein solid chemical components with a size of more than 10 micrometers are held back, wherein the membrane is wholly or partly embodied as a porous material that is permeable to at least one of the sample and components of the sample, wherein the membrane lies directly on the test field such that no interspace, or an interspace of 5 μm or less, is produced between the test field and the membrane.

8. The analytic magazine according to claim 7, wherein the test field is at least partly covered by the membrane.

9. The analytic magazine according to claim 7, wherein the membrane has a mean pore dimension of between 1 μm and 10 μm.

10. The analytic magazine according to claim 7, wherein the membrane has a thickness of between 30 μm and 150 μm.

11. The analytic magazine according to claim 7, wherein the membrane has one or more of the following materials: a cellulose, a polysulfone, a nylon, a polyvinylidene fluoride, a regenerated cellulose, and a hydrophilic polyurethane.

12. The analytic magazine according to claim 7, wherein the membrane has at least one structuring with at least one passage area, which is at least partly permeable to the sample of the bodily fluid, and with at least one impermeable area that is at least partly impermeable to the sample of the bodily fluid.

13. The analytic magazine according to claim 12, wherein the analytic magazine has a plurality of chambers, wherein the membrane has a common form for a number of chambers, and in each case provides at least one passage area for the number of chambers.

14. The analytic magazine according to claim 7, wherein the analytic magazine has a housing with at least one opening facing the chamber, wherein the membrane is applied to the opening from the outside and is accessible from the chamber through the opening.

15. The analytic magazine according to claim 14, wherein the membrane is connected to the housing by at least one connection, which comprises one or more of the following connections: a welded joint or a connection produced by heat staking, an ultrasound welded joint, or a laser welded joint; and a bonded connection.

16. The analytic magazine according to claim 14, wherein the test field is connected to the housing by at least one of a force-fit and an interlocking connection.

17. A method for producing an analytic magazine, wherein the analytic magazine comprises at least one chamber with at least one analytic aid, wherein the analytic aid comprises at least one test element for detecting at least one analyte in a sample of a bodily fluid, wherein the test element comprises at least one test field with at least one test chemical, wherein at least one lancet is introduced into the chamber, wherein the method furthermore comprises the following steps:
at least one housing part of a housing of the analytic magazine is produced;
the test field is produced; and
at least one of the test field and the test element is connected to the housing part such that the test field is partly accessible from the chamber for placing a sample, wherein at least one wall of the chamber partly covers the test field and thereby delimits a test-field surface of the at least one test field having the at least one test chemical that is accessible from the chamber, wherein the test-field surface is delimited by virtue of the fact that the wall of the chamber lies directly on the test-field surface along one or more delimitation lines or lies in the vicinity of the test-field surface such that a region of the test-field surface that is not covered by the wall is accessible to the sample, but, by contrast, a region covered by the wall is not.

* * * * *